(12) United States Patent
O'Connor et al.

(10) Patent No.: US 7,939,530 B2
(45) Date of Patent: May 10, 2011

(54) TREATMENT OF LYMPHOMA USING 10-PROPARGYL-10-DEAZAAMINOPTERIN AND GEMCITABINE

(75) Inventors: Owen A O'Connor, Scarsdale, NY (US); Francis Sirotnak, Hampton Bays, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 1115 days.

(21) Appl. No.: 11/568,254

(22) PCT Filed: May 31, 2005

(86) PCT No.: PCT/US2005/019170
§ 371 (c)(1),
(2), (4) Date: Feb. 20, 2007

(87) PCT Pub. No.: WO2005/117892
PCT Pub. Date: Dec. 15, 2005

(65) Prior Publication Data
US 2008/0058280 A1   Mar. 6, 2008

Related U.S. Application Data

(60) Provisional application No. 60/521,593, filed on May 30, 2004.

(51) Int. Cl.
*A61K 31/519* (2006.01)
*C07D 475/08* (2006.01)
(52) U.S. Cl. .................................. 514/249; 544/260
(58) Field of Classification Search .................. None
See application file for complete search history.

(56) References Cited

U.S. PATENT DOCUMENTS

| 5,354,751 | A  | * | 10/1994 | DeGraw et al. | |
|---|---|---|---|---|---|
| 6,323,205 | B1 | * | 11/2001 | Sirotnak et al. | |
| 7,622,470 | B2 | * | 11/2009 | O'Connor et al. | 514/249 |
| 2005/0267117 | A1 | * | 12/2005 | O'Connor et al. | 514/251 |

FOREIGN PATENT DOCUMENTS
WO    98/02163    *    1/1998

OTHER PUBLICATIONS

Tonkinson et al., "Cell Cycle Modulation by a Multitargeted Antifolate, LY231514, Increases the Cytotoxicity and Antitumor Activity of Gemcitabine in HT29 Colon Carcinoma" Cancer Research (1999) vol. 59 pp. 3671-3676.*
Giovanetti et al., "Synergistic Cytotoxicity and Pharmacogenetics of Gemcitabine and Pemetrexed Combination in Pancreatic Cancer Cell Lines" Clinical Cancer Research (2004) vol. 10 pp. 2936-2943.*
Teicher et al., "Treatment Regimens Including the Multitargeted Antifolate LY231514 in Human Tumor Xenografts"Clinical Cancer Research (2000) vol. 6 pp. 1016-1023.*
Akutsu M et al. "Schedule-dependent synergism and antagonism between methotrexate and cytarabine against human leukemia cell lines in vitro." Leukemia. Mar. 12, 2002, pp. 1808-1817. vol. 16.
Cadman Ed et al. "Mechanism of Synergistic Cell Killing when Methotrexate Precedes Cytosine Arabinoside." J. Clin Invest. 1979. pp. 788-797. vol. 64.
Chau I et al. "Gemcitibine and its combinations in the treatment of malignant lymphoma." Clincal Lymphoma. 2002. pp. 97-104. vol. 3, No. 11.
DeGraw et al. "Synthesis and Antitumor Activity of 10-Propargyl-10-deazaanninopterin." Journal of Medical Chemistry. 1993. pp. 2228-2231. vol. 36.
Hoovis ML et al. "Enhancement of the Antiproliferative Action of 1-β-D-Arabinofuranosylcytosine by Methotrexate in Murine Leukemic Cells (L5178Y)." Cancer Research. 1973. pp. 521-525. vol. 33.
Khokhar Nushima et al. "Experimental Therapeutices with a New 10-Deazaaminopterin in Human Mesothelioma: Further Improving Efficacy through Structural Design, Pharmacologic Modulation at the Level of MRP ATPases, and Combines Therpay with Platinums." Clinical Cancer Research. 2001. pp. 3199-3205. vol. 7.
Krug Lee et al. "10-propargyl-10-deazaaminopterin: an antifolate with activity in patients with previously treated non-small cell lung cancer." Clinical Cancer Research: An official journal of the American Association for Cancer Research 2003. pp. 2072-2078. vol. 9, No. 6.
Sirotnak F.M. et al. "Co-administration of Probenecid, an Inhibitor of a cMOAT/MRP-like Plasma Membrane ATPase, Greatly Enhanced the Efficacy of a New 10-Deazaaminopterin against Human Solid Tumors in Vivo." Clinical Cancer Research. 2000. pp. 3705-3712. vol. 6.
Vrhovac Radovan et al. "A novel antifolate 10-propargyl-10-deazaaminopterin (PDX) displays synergistic effects with gemcitabine in non-Hodgkin's lymphoma models in vitro and in vivo." 45th Annual Meeting of the American Society of Hematology. Nov. 16, 2003. pp. 288b. vol. 102, No. 11.
Wang E S et al. "Activity of a novel anti-folate (PDX, 10 propargyl-10-deazaaminopterin) against human lymphoma is superior to methotrexate and correlates with tumor RFC-1 gene expression." Leukemia and Lymphoma. Jun. 1, 2003. pp. 1027-1035. vol. 44, No. 6.
Wang et al."PDX, a Novel Antifolate with Potent in Vitro and in Vivo Activity in Non-Hodgkin's Lymphoma." Developmental Hematology and the program for Molecular Pharmacology and Experimental Therapeutics. Abstract 2565.

* cited by examiner

*Primary Examiner* — Eric S Olson
(74) *Attorney, Agent, or Firm* — Larson & Anderson, LLC

(57) ABSTRACT

Lymphoma is treated using therapeutic combinations of PDX and gemcitabine by administering to a patient suffering from lymphoma a therapeutically effective amount of PDX in combination with a therapeutically effective amount of gemcitabine. The two agents can be administered together or in either order, although administration of PDX followed by gemcitabine is preferred. As in the case of MTX and Ara-C, synergism is observed, but the extent of the synergism is greater. Further, test results indicate that mechanism of action for combinations of PDX and Gem is different than for MTX and Ara-C, with more emphasis on induction of apoptosis.

15 Claims, 3 Drawing Sheets

TREATMENT OF LYMPHOMA USING 10-PROPARGYL-10-DEAZAAMINOPTERIN AND GEMCITABINE

This application is a national stage under 35 USC §371 of PCT/US2005/019170, filed May 31, 2005, which claims priority from U.S. Provisional Application No. 60/521,593, filed May 30, 2004. The provisional application is incorporated herein by reference.

STATEMENT CONCERNING GRANT SUPPORT

This application was supported by NH grant numbers CA092074 and CA 0172(00). The US government may have certain rights in this invention.

BACKGROUND OF THE INVENTION

This application relates to the use of a combination of 10-propargyl-10-deazaminopterin and gemcitabine in the treatment of lymphoma.

10-Propargyl-10-deazaminopterin ("PDX") is a member of a large class of compounds which have been tested and in some cases found useful in the treatment of tumors. This compound, which has the structure shown in FIG. 1, was disclosed by DeGraw et al., "Synthesis and Antitumor Activity of 10-Propargyl-10-deazaminopterin," *J. Medical Chem.* 36: 2228-2231 (1993) and shown to act as an inhibitor of growth in the murine L1210 cell line and to a lesser extent of the enzyme dihydrofolate reductase ("DHFR"). In addition, some results were presented for the antitumor properties of the compound using the E0771 murine mammary tumor model. This data was equivocal because of the small number of mice used in the test (3 per dosage), the absence of any standard deviation information which would quantify the reliability of the data, and the fact that the highest dose used was in fact toxic to the mice. Nevertheless, assuming this data has some predictive value for the efficacy of a drug in treating human tumors, it would at best predict a drug which, at equivalent levels of tolerance, had properties comparable to or perhaps slightly better than methotrexate.

PCT Publication No. WO98/02163, discloses the surprising observation that more highly purified PDX compositions when tested in a xenograft model for their efficacy against human tumors have now been shown to be far superior to methotrexate ("MTX") and are even superior to edatrexate ("ETX"), a more recent clinical candidate. Moreover, 10-propargyl-10 dAM showed a surprising ability to cure tumors such that there was no evidence of tumor growth several weeks after the cessation of therapy. Thus, highly purified composition containing 10-propargyl-10 dAM. can be used in accordance with the invention to treat tumors, including both solid tumors and leukemias. The composition is illustrated for use in treatment of human mammary tumors and human lung cancer.

Subsequent studies on PDX have shown that it is useful on its own and in combinations with other therapeutic agents. For example, Sirotnak et al., Clinical Cancer Research Vol. 6, 3705-3712 (2000) reports that co-administration of PDX and probenecid, an inhibitor of a cMOAT/MRP-like plasma membrane ATPase greatly enhances the efficacy of PDX against human solid tumors in vivo. PDX and combinations of PDX with platinum based chemotherapeutic agents have been shown to be effective against mesothelioma. (Khokar, et al., Clin. Cancer Res. 7: 3199-3205 (2001).

Gemcitabine (Gem), also referred to as 1-(2',2'-difluoro-β-D-arabinofuranosyl) cytosine or 2',2'-difluorodeoxycytidine, is a known compound that belongs to the group of medicines called antimetabolites. It is used to treat various types of cancer, including cancer of the breast, pancreas and lung. Gemcitabine is sold under the tradename GEMZAR.

A variety of in vitro and in vivo experiments have demonstrated that sequential methotrexate (MTX) and cytarabine (Ara-C) are synergistic compared to the single agents or alternative schedules. As early as 1973, Hoovis and Chou demonstrated that MTX and Ara-C exhibited marked synergy in a murine leukemia cell line (L5178Y) when used in a sequence dependent fashion. (Hoovis M L, Chou M Y. Enhancement of the antiproliferative action of 1--D-arabinofuranosylcytosine by methotrexate in murine leukemic cells (L5178Y). Cancer Res. 1973; 33:521-5.). The authors demonstrated that the pretreatment with MTX significantly increased the level of ara-CTP independent of DNA synthesis, which led to increased incorporation into RNA, and enhanced cytotoxicity. Cadman and Eiferman, Mechanism of synergistic cell killing when methotrexate precedes cytosine arabinoside: study of L1210 and human leukemic cells. J. Clin. Invest. 1979; 64:788-97, similarly demonstrated the sequence dependency of MTX and Ara-C in the L1210 model of myeloid leukemia, confirming the preferential accumulation of ara-CTP in MTX pretreated cells. Using the classic isobologram method of Steel and Peckham, Akutsu et al., Schedule-dependent synergism and antagonism between methotrexate and cytarabine against human leukemia cell lines in vitro. Leukemia 2002; 16:1808-17, recently demonstrated that the ordered treatment of MTX followed by Ara-C is truly synergistic in a mathematical analysis, while other schedules of administration (for example, given together) were potentially antagonistic. MTX followed by Ara-C is currently a treatment of choice for lymphoma.

SUMMARY OF THE INVENTION

In accordance with the present invention, lymphoma is treated using therapeutic combinations of PDX and GEM. Thus, in accordance with one aspect of the invention, a method is provided for the treatment of lymphoma comprising administering to a patient suffering from lymphoma a therapeutically effective amount of PDX in combination with a therapeutically effective amount of gemcitabine. The two agents can be administered together or in either order, although administration of PDX followed by gemcitabine is preferred. As in the case of MTX and Ara-C, synergism is observed, but the extent of the synergism is greater. Further, test results indicate that mechanism of action for combinations of PDX and Gem is different than for MTX and Ara-C, with more emphasis on induction of apoptosis.

DETAILED DESCRIPTION OF THE INVENTION

This application relates to the use of combination of 10-propargyl-10-deazaminopterin and gemcitabine in the treatment of lymphoma.

As used in the specification and claims of this application, the term "lymphomas" refers to Non-Hodgkins Lymphoma (NHL); diffuse large B-cell lymphoma (DLBCL); follicular lymphoma (FL); Hodgkin's Disease; Burkitt's Lymphoma; cutaneous T cell lymphoma; primary central nervous system lymphoma, and lymphomatous metastases.

In one embodiment of the invention, the composition comprises "highly purified" PDX. As used in the specification and claims hereof, compositions which are "highly purified" contain PDX substantially free of other folic acid derivatives, particularly 10-deazaminopterin, which can interfere with the antitumor activity of the PDX. A composition within the scope of the invention may include carriers or excipients for formulating the PDX into a suitable dosage unit form for therapeutic use, as well as additional, non-folate therapeutic agents.

PDX can be synthesized using the method disclosed in the DeGraw paper, supra or in Example 7 of U.S. Pat. No. 5,354,751, which is incorporated herein by reference. HPLC evaluation of the product prepared by this method shows the presence of a substantial amount (~4.6%) of an impurity A (FIG. 2) which has a retention time consistent with 10-deazaminopterin. Thus, if this synthetic approach is employed further purification is necessary beyond that disclosed in the DeGraw et al. paper. Such purification can be carried out by additional HPLC or crystallization to remove the 10-deazaminopterin and other folic acid derivatives which may be present.

Figure 1:
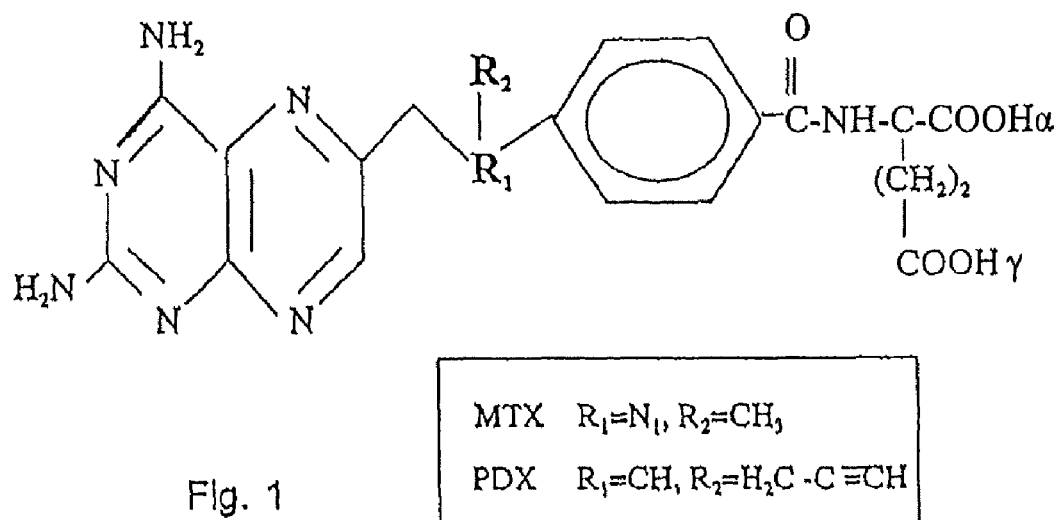
FIG. 1 shows the structure of PDX and methotrexate.
Figures 2, 3:
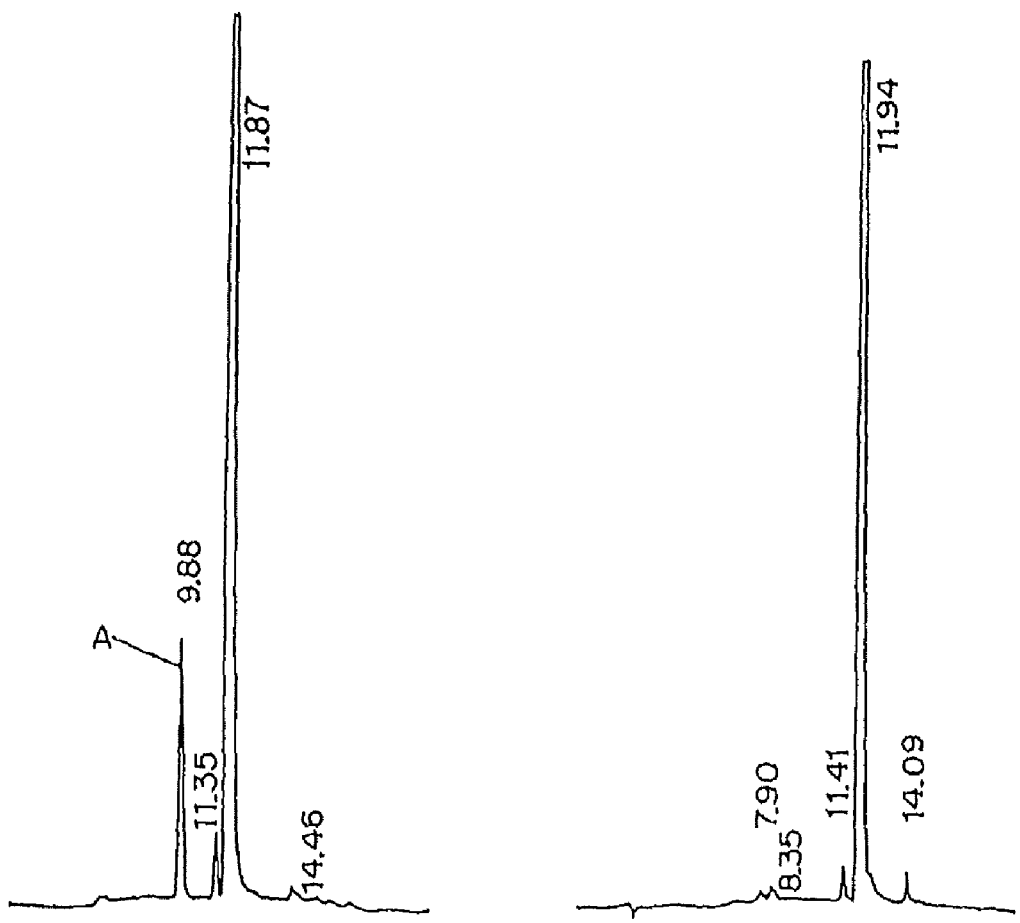
FIG. 2 shows an HPLC of an impure 10-propargyl-10 dAM preparation prepared in accordance with the prior art.
FIG. 3 shows an HPLC of a highly purified PDX preparation in accordance with the invention.

FIG. 3 shows an HPLC of a highly purified preparation consisting essentially of 10-propargyl-10 dAM in accordance with the invention prepared using the method described in Example 1. In this case, the amount of PDX (as determined by HPLC peak area) approaches 98%, and the peak corresponding to 10-deazaminopterin is not detected by the processing software although there is a minor baseline ripple in this area.

As set forth in greater detail in the examples herein, combination therapy using PDX and gemcitabine has been tested in vitro and in in vivo model systems for efficacy against lymphoma. Table 1 sets forth data obtained in a cytotoxicity assay (Example 2) using SKI-DLCL-1 lymphoma cells. SKI-DLCL-1 is a diffuse large b cell lymphoma (DLBCL) cell line that is particularly resistant to PDX. This line is known to have the lowest level of RFC-1 expression on its surface as demonstrated by RT-PCR (rendering it more resistant than lines with greater RFC-1 expression), demonstrates an $EC_{50}$ roughly 2 to 3 fold greater than other B-cell lymphoma cell lines, and is associated with the fewest number of complete remissions in the in vivo SCID models (30% vs 90%).

In Table 1, the additive effect is in each case the % of control for the single agents multiplied together. The expected additive effect for PDX+Gem is better than for MTX and ara-C, because the agents are individually better. What is observed for both MTX/AraC combinations and PDX/Gem combinations is that the actual result is better than the predicted additive result. The extent of this synergism is quantified in Table 1 as (actual-additive)/additive so that the amount of reduction that occurs through the use of the combination is expressed as a percentage of the expected additive benefit. What this shows is that the enhancement or synergism that is observed using PDX/Gem combinations is substantially greater than what would be predicted based on the MTX-AraC results.

TABLE 1

| Drug | Raw IC50 | fraction of control | additive | synergy (% of additive) |
|---|---|---|---|---|
| control | 25 | 1 | | |
| MTX | 23 | 0.92 | | |
| Ara-C | 19 | 0.76 | | |
| MTX + AraC | 11 | 0.44 | 0.699 | 37 |
| MTX->AraC | 8 | 0.32 | 0.699 | 54 |
| AraC->MTX | 11.5 | 0.46 | 0.699 | 34 |
| PDX | 21 | 0.84 | | |
| Gem | 18 | 0.72 | | |
| PDX + Gem | 6 | 0.24 | 0.605 | 60 |
| PDX->Gem | 3.5 | 0.14 | 0.605 | 77 |
| Gem->PDX | 6 | 0.24 | 0.605 | 60 |

While not intending to be bound by any particular mechanism, it is believed that this difference may arise because the mechanism by which PDX and Gem function is different from the mechanism for MTX and Ara-C notwithstanding the similar labels (i.e. antifolate or cytidine analog) applied to the compounds.

Table 2 shows results for a test on induction of apoptosis in SKI-DLCL-1 cells following exposure to MTX. Ara-C, PDX and Gem in combined and scheduled exposures. In each case, the total exposure time was 72 hours. In sequential treatments, the first drug was administered 24 hours prior to the second drug.

TABLE 2

| Treatment | % change in apoptosis |
|---|---|
| control - no treatment | 0 |
| MTX | −12.24 |
| Ara-C | −3.08 |
| MTX + AraC | −3.17 |
| MTX -> Ara-C | 0.32 |
| PDX | 28.21 |
| GEM | 33.76 |
| PDX + GEM | 10.65 |
| PDX->GEM | 52.58 |

As shown, the extent to which the treatment regimens induce apoptosis is markedly different. The results for Gem followed by PDX were the same as for PDX+GEM.

Table 3 shows results for caspase 3 activation in SKI-DLCL-1 cells following exposure to MTX. Ara-C, PDX and Gem in combined and scheduled exposures.

TABLE 3

| Treatment | Fluorescence at 485ex/527em | Difference from control |
|---|---|---|
| control - no treatment | 134.3 | |
| MTX (1 nM) | 131 | −3.3 |
| Ara-C (1 nM) | 141.1 | 6.8 |
| MTX + AraC | 157.2 | 22.9 |
| MTX -> Ara-C | 158.8 | 24.5 |
| PDX | 265.5 | 131.2 |
| GEM | 195.4 | 61.1 |
| PDX + GEM | 248.2 | 113.9 |
| PDX->GEM | 307.9 | 173.6 |

As shown, the extent to which the treatment regimens induce caspase 3 is markedly different with PDX/GEM treatments leading to greater caspase 3 induction. The results for Gem followed by PDX were the same as for PDX+GEM.

Studies of the cell cycle following the various treatments as described above yielded essentially the same percentage of cells in G1 arrest. However, the fraction of cells in S-phase was variable, with the fewest in those samples treated with Gem. Remarkably, while the number of cells in G2 is relative similar among all the groups (9 to 15%), there are no cells in G2 in the group treated with PDX followed by Gem (0%). For example, the percentage of cells in G2 in the control were about 12%, which was not significantly different from that noted in cells treated with MTX, PDX, Gem or Ara-C alone (9 to 15%). The cells treated with the scheduled administration of PDX followed by Gem were the only ones to demonstrate a complete absence of cells in G2, with a proportionately greater number of cells exhibiting S phase arrest compared to any other treatment consideration. This accumulation of cells in S phase in the PDX->Gem treated cells may enhance the sensitivity of the cell to the cytotoxic effect of the cytidine analog. These data also indicate that this particular combination (PDX->Gem) is more effective at inducing a G1/S arrest compared to other treatment exposure groups, which may explain the greater degree of apoptosis noted in the earlier experiments.

PDX followed by Gem is also markedly superior to all other treatment groups in vivo. The superiority of PDX over MTX in in vivo lymphoma models across many different cell lines including HT, RL, SKI-DLCL-1 and a Burkitt's cell line (Raji) has been demonstrated. (See Example 2). Given the experience that SKI-DLCL-1 is the most PDX resistant line in the panel, it was selected for these in vivo synergy experiments. In all xenograft experiments, animals in the control group demonstrated rapid POD and had to be sacrificed early secondary to tumor growth. All animals were treated with the maximum tolerated dose (MTD) of each drug, save the combination studies. A preliminary xenograft experiment using irradiated NOD-SCID mice with subcutaneous tumors of SKI showed that mice treated with PDX or Gem at 60 mg/kg initially responded to treatment but by day 44 regrew tumors to 739% and 318% of their initial tumor volumes, respectively. Those animals treated with MTX at 40 mg/kg (MTD) or Ara-C at 300 mg/kg (MTD) or in combination at one-half the MTD of these drugs displayed modest growth delay compared to the control, with all animals in these groups having to be sacrificed due to excessive tumor volume by week three. Animals treated in the combination experiments with one-half the MTD of PDX and Gem (30 mg/kg each) experienced significant reduction (63.1%) of their initial tumor volume, with 3 animals achieving a complete remission, one a partial remission, and one developed disease progression.

Figure 5:
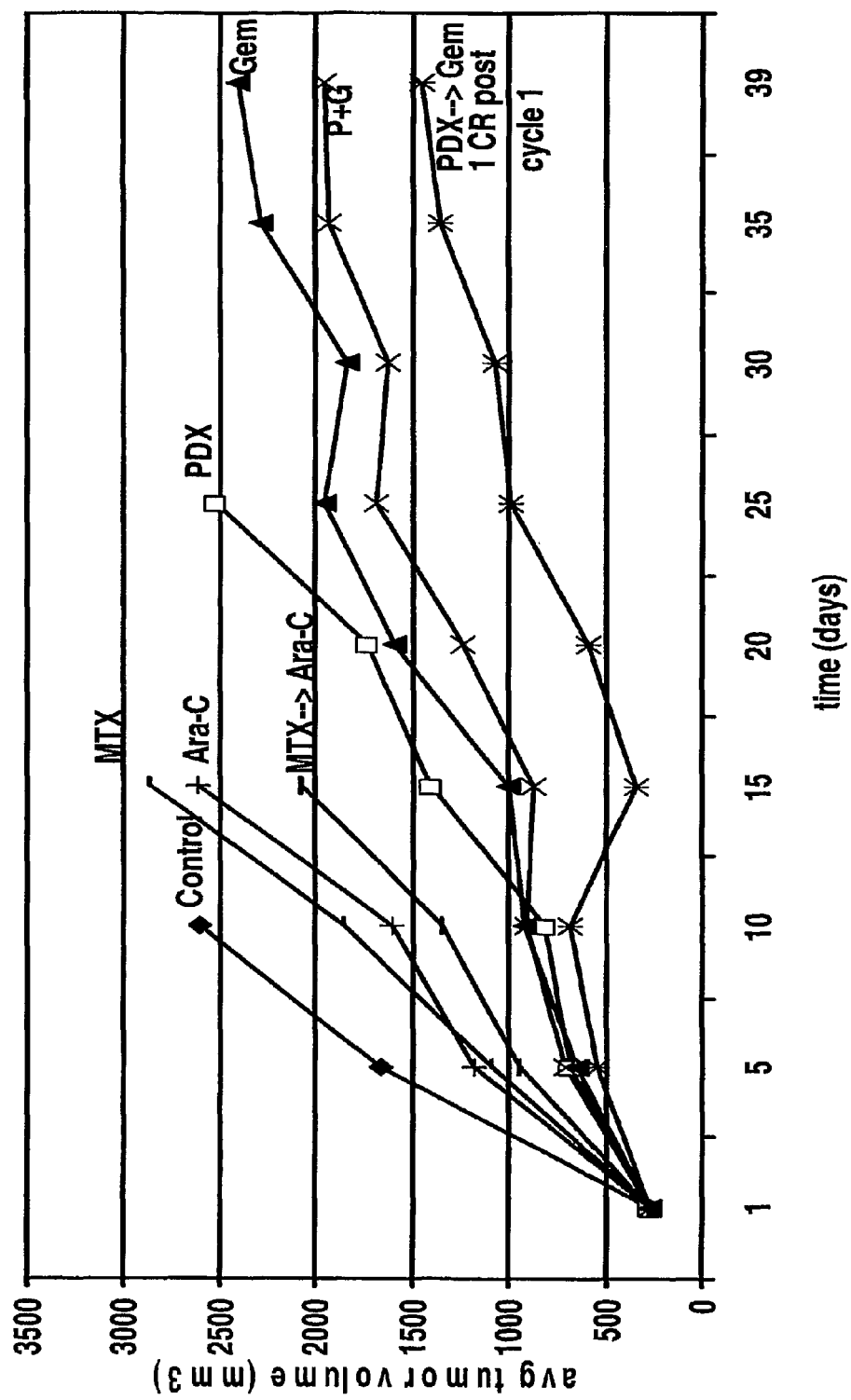
FIG. 5 shows results from tests on an in vivo SCID beige mouse xenograft model of SKI-DLBCL-1.

In order to explore how low a dose of PDX and Gem could be used before losing the potential synergy, a second xenograft experiment was conducted using one-quarter of the MTD of PDX and Gem (15 mg/kg). A similar dose reduction for MTX and Ara-C was not performed given the lack of activity seen at the higher doses. Interestingly, the patterns appreciated in the earlier experiment were recapitulated in the second experiment. Again, control groups had to be sacrificed early due to excessive tumor growth, as did animals receiving MTX (60 mg/kg) alone, Ara-C (300 mg/kg) alone, or both drugs in combination. These data demonstrated that even using one-quarter of the MTD of PDX and Gem given in a ordered fashion was markedly more efficacious that any MTX or Ara-C treated cohort. Though fewer complete remissions were noted, still, a complete remission was only observed in those animals receiving PDX followed by Gem (FIG. 5). These in vivo experiments clearly establish the marked superiority of PDX and Gem when given in a sequential fashion, even in a cell line noted to be historically among the most resistant in the collection to PDX and MTX.

Tumors resected from all mice receiving MTX, Ara-C, PDX or Gem in a schedule dependent manner revealed minimal activation of caspase 3 in the tissue of mice treated with saline (i.e. control), any single agent, and the doublet of MTX and Ara-C. Interestingly, the most significant staining for activated caspase 3 occurred in those samples of tumor in mice treated with PDX followed by Gem. These data are concordant with the observations from the in vitro experiments and apoptosis assays (Tables 1 and 2) which also demonstrated the most significant activation of caspase 3 in cells treated with PDX followed by Gem.

For use in the present invention, PDX is advantageously formulated as part of a pharmaceutical preparation. The specific dosage form will depend on the method of administration, but may include tablets, capsules, oral liquids, and injectable solutions for intravenous, intramuscular or intraperitoneal administration. As described below (Example 8), a Phase I and Pharmakokinetic study has been conducted. Based on this study, a preferred dosing schedule involves the administration of 150 mg/m$^2$ every two weeks. Lower levels may of course be indicated depending on the tolerance of an individual patient, or if more frequent administration were adopted. For example, levels on the order of 40 to 120 mg/m$^2$ of body surface area/day are appropriate. Dosages of 30 mg/m$^2$ weekly for 3 weeks followed by a one week rest, 30 mg/m$^2$ weekly×6 weeks followed by a one week rest, or gradually increasing doses of PDX on the weekly×6 week schedule are also suitable. Similarly, higher levels could be utilized if less frequent administration were used. Thus, in a general sense, dosages of 30 to 275 mg/m$^2$ are suitably used with various dosing schedules, for example 135 to 275 mg/m$^2$ for biweekly dosages, and 30 to 150 mg/m$^2$ for weekly dosages. The determination of suitable dosages using protocols similar to those described in U.S. Pat. No. 6,323,205, which is incorporated herein by reference, is within the skill in the art.

PDX is used in the present invention in therapeutic combination with gemcitabine. In addition, PDX and gemcitabine may be used in combinations with other cytotoxic and anti-tumor compounds, including vinca alkaloids such as vinblastine, navelbine and vindesine; probenicid, nucleotide analogs such as 5-fluorouracil, and cytarabine; alkylating agents such as cyclophosphamide or ifosfamide; cisplatin or carboplatin; leucovorin; taxanes such a paclitaxel or docetaxel; anti-CD20 monoclonal antibodies, with or without radioisotopes, and antibiotics such as doxorubicin and mitomycin. Combinations of PDX with several of these other antitumor agents or with growth factor inhibitors and anti-angiogenic agents may also be used.

PDX and gemcitabine may be concurrently administered or utilized in combination as part of a common treatment regimen, in which the PDX and the gemcitabine are administered at different times. For example, the gemcitabine may be administered before, immediately afterward or after a period of time (for example 24 hours) relative to the PDX administration. Thus, for purposes of this application, the term administering refers generally to concurrent administration or to sequential administration of the drugs and in either order in a parallel treatment regimen with or without a separation in time between the drugs unless otherwise specified. PDX and Gem are suitably administered using known and standard protocols for the drugs individually, although lower dosages than used in individual treatments may be suitable given the synergistic activity of the two therapeutic agents.

The present invention also provides a method for assessing sensitivity of a lymphoma to treatment with 10-propargyl-10-deazaminopterin comprising the steps of (a) obtaining a sample of the lymphoma;

(b) determining the amount of reduced folate carrier-1 enzyme (RFC-1) expressed by the sample, wherein a higher level of expressed RFC-1 is indicative of greater sensitivity to 10-propargyl-10-deazaminopterin; and (c) generating a report of the sensitivity of the sample to 10-propargyl-10-deazaminopterin. This method is described in Example 6 of this application.

Example 1

Figure 4:
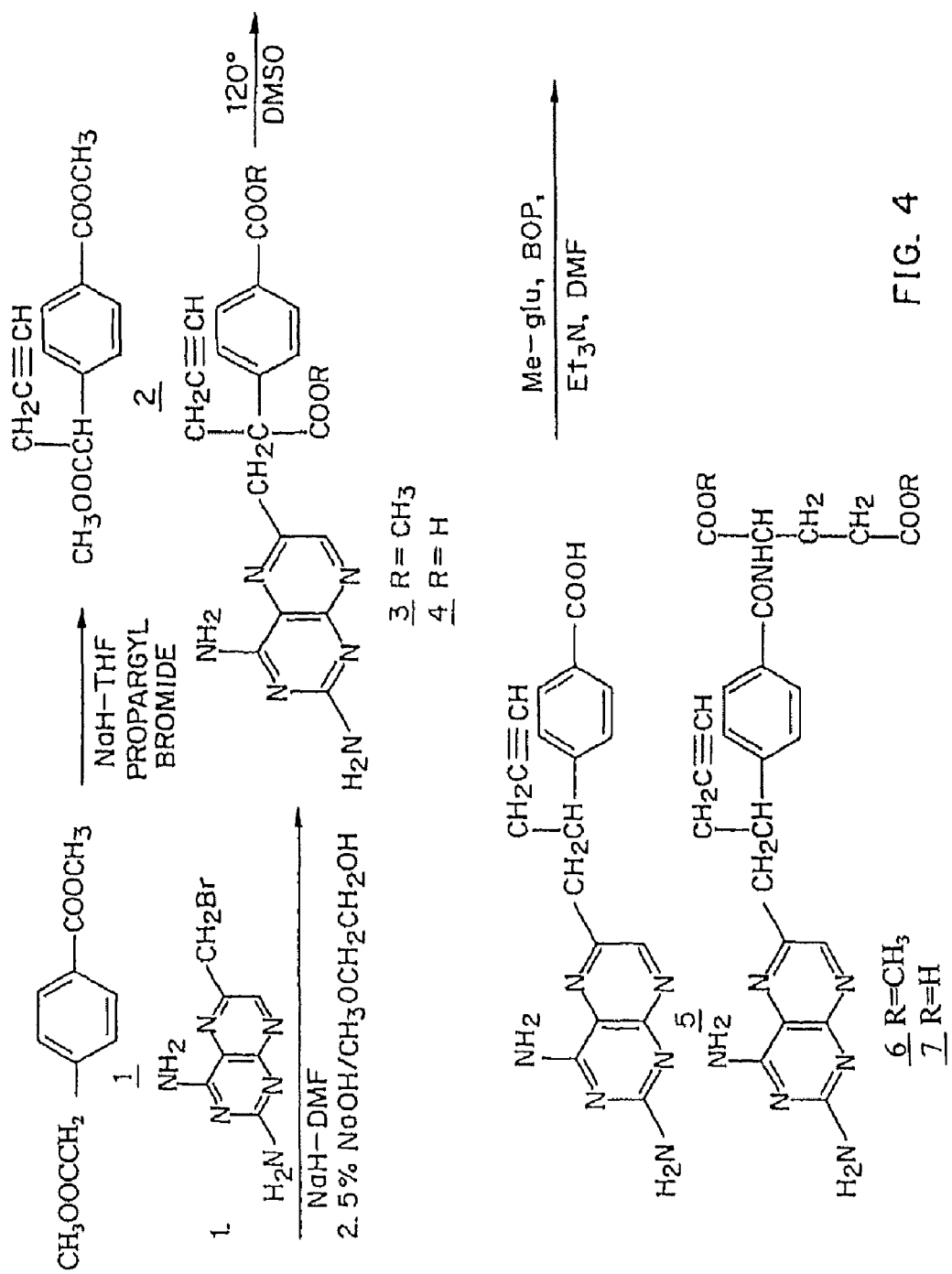
FIG. 4 shows a synthetic scheme useful in preparing the compound in accordance with the invention.

FIG. 4 shows a synthetic scheme useful in preparing 10-propargyl-10-dAM in accordance with the invention. A mixture of 60% NaH in oil dispersion (1.06 g, 26.5 mmol) in 18 mL of sieve-dried THF was cooled to 0° C. The cold mixture was treated with a solution of homoterephthalic acid dimethyl ester (5.0 g, 24 mmol. compound 1 in FIG. 4) in dry THF (7 mL), and the mixture was stirred for 1 hour at 0° C. Propargyl bromide (26.4 mmol) was added, and the mixture was stirred at 0° C. for an additional 1 hour, and then at room temperature for 16 hours. The resulting mixture was treated with 2.4 mL of 50% acetic acid and then poured into 240 mL of water. The mixture was extracted with ether (2×150 mL). The ether extracts were combined, dried over $Na_2SO_4$, and concentrated to an orange-yellow oil. Chromatography on silica gel (600 mL of 230-400 mesh) with elution by cyclohexane-EtOAc (8:1) gave the product α-propargylhomoterephthalic acid dimethyl ester (compound 2) as a white solid (4.66) which appeared by TLC (cyclohexane-EtOAc, 3:1) to be homogeneous. Mass spectral data on this product, however, showed it to be a mixture of the desired product 2, and the dipropargylated compound. No starting material 1 was detected. HPLC shows the ratio of mono- to di-propargylated products to be about 3:1. Since the dipropargylated product, unlike compound 1, cannot produce an unwanted coproduct in the next step of the reaction, this material was suitable for conversion to compound 3. Absence of starting compound 1 in the product used to proceed in the synthesis is very important in order to avoid the sequential formation of 10-dAM during the transformations lading to the final product, because complete removal from 10-dAM from 10-propargyl-1-dAM is very difficult.

A mixture was formed by combining 0.36 g of a 60% NaH (9 mmol) in oil dispersion with 10 mL of dry DMF and cooled to 0-5° C. The cold mixture was treated drop-wise with a solution of the product of the first reaction (compound 2) (2.94 g, 12 mmol) in 10 mL dry DMF and then stirred at 0° C. for 30 minutes. After cooling to −25° C., a solution of 2,4, diamino-6-(bromomethyl)-pteridine hydrobromide-0.2 2-propanol (1.00 g, 2.9 mmol) in 10 mL dry DMF was added drop-wise while the temperature was maintained near −25° C. The temperature of the stirred mixture was allowed to rise to −10° C. over a period of 2 hours. After an additional 2 hours at −10° C., the temperature was allowed to rise to 20° C.; stirring at room temperature was continued for 2 hours longer. The reaction was then adjusted to pH 7 by addition of solid $CO_2$, After concentration in vacuo to remove solvent, the residue was stirred with diethyl ether and the ether insoluble material was collected, washed with water, and dried in vacuo to give 1.49 g of a crude product. This crude product was dissolved in $CHCl_3$-MeOH (10:1) for application to a silica gel column. Elution by the same solvent system afforded 10-propargyl-10-carbomethoxy-4-deoxy-4-amino-10-deazapteroic acid methyl ester (compound 3) which was homogenous to TLC in 40% yield (485 mg).

A stirred suspension of compound 3 (400 mg, 0.95 mmol) in 2-methoxyethanol (5 mL) was treated with water (5 mL) and then 10% sodium hydroxide solution (3.9 mL). The mixture was stirred as room temperature for 4 hours, during which time solution occurred. The solution was adjusted to pH 8 with acetic acid and concentrated under high vacuum. The resulting residue was dissolved in 15 mL of water and acidified to pH 5.5-5.8 resulting in formation of a precipitate. The precipitate was collected, washed with water and dried in vacuo to recover 340 mg of compound 4 (91% yield). HPLC analysis indicated a product purity of 90%.

Compound 4 (330 mg) was decarboxylated by heating in 15 mL DMSO at 115-120° C. for 10 minutes. A test by HPLC after 10 minutes confirmed that the conversion was essentially complete. DMSO was removed by distillation in vacuo (bath at 40° C.). The residue was stirred with 0.5 N NaOH to give a clear solution, Acidification to pH 5.0 with 1N HCl gave 10-propargyl-4-deoxy-4-amino-10-deazapteroic acid (compound 5) as a yellow solid in 70% yield. HPLC indicated product purity at this stage as 90%.

Compound 5 (225 mg, 0.65 mmol) was coupled with dimethyl L-glutamate hydrochloride (137 mg, 0.65 mmol) using BOP reagent (benzotriazole-1-yloxytris(dimethylamino) phosphonium hexafluorophosphate (287 mg, 0.65 mmol, Aldrich Chemical Co.) in DMF (10 mL) containing triethylamine (148 mg, 1.46 mmol). The mixture was stirred for 3 hours at 20-25° C. and then evaporated to dryness. The residue was stirred with water, and the water-insoluble crude product was collected and dried in vacuo. The crude product (350 mg) was purified by silica gel chromatography with elution by $CHCl_3$-MeOH (10:1) containing triethylamine (0.25% by volume) to recover 165 mg of 10-propargyl-10-deazaminopterin dimethyl ester (compound 6, 50% yield) which was homogeneous to TLC($CHCl_3$-MeOH 5:1).

Compound 6 (165 mg, 0.326 mmol) was suspended in 10 mL stirred MeOH to which 0.72 mL (0.72 meq) 1N NaOH was added. Stirring at room temperature was continued until solution occurred after a few hours. The solution was kept at 20-25° C. for 8 hours, then diluted with 10 mL water. Evaporation under reduced pressure removed the methanol, and the concentrated aqueous solution was left at 20-25° C. for another 24 hours. HPLC then showed the ester hydrolysis to be complete. The clear aqueous solution was acidified with acetic acid to pH 4.0 to precipitate 10-propargyl-10-deazaaminopterin as a pale yellow solid, The collected, water washed and dried in vacuo product weighed 122 mg (79% yield). Assay by elemental analysis, proton NMR and mass spectroscopy were entirely consistent with the assigned structure. HPLC analysis indicated purity of 98% and established the product to be free of 10-deazaminopterin.

Example 2

A PDX preparation prepared in accordance with Example 1 and an MTX preparation were tested for cytotoxicity against a panel of five human lymphoma cell lines. Experiments were performed as described previously. (Sirotnak et al., Cancer Chemother. Pharmacol. 12: 18-25 (1984). In brief, 2.5 to 5×10³ cells were plated per well in 96-well flat bottom plates. Drug was added in a 0.9% NaCl solution (pH 7.0) over a range of concentrations, and cells were continuously exposed to drug for 5 days. Colorimetric dye (XTT or Alamar blue) was added for an addition period of time (XTT dye, 6 hours, Alamar blue, 24 hours). Each plate was then read on an automated plate reader at 590 nm. The percentage of inhibition was calculated as growth of cells exposed to drug divided by growth of controls (cells incubated with media only). $IC_{50}$ values were determined as the drug concentrations at which cell growth was inhibited 50% as compared to controls. Experiments were repeated as lest three times. Experiments were also conducted with continuous drug exposures lasting for 3 and 4 days with results similar to the 5 day results.

The results of the study with 5 day drug exposures is summarized in Table 3. As shown, in every instance, the $IC_{50}$ of PDX was substantially lower than the $IC_{50}$ for MTX, indicating greater efficacy and/or the ability to use lower and therefore less toxic amounts to achieve the same efficacy.

TABLE 3

Relative growth inhibition in vitro

| Cell Line | Lymphoma Type | $IC_{50}$ PDX (nM) | $IC_{50}$ MTX (nM) |
|---|---|---|---|
| Hs445 | Hodgkin's disease | 1.6 ± 0.8 | 32 ± 2.2 |
| HT | Diffuse large B cell | 2.0 ± 0.4 | 35 ± 5.0 |
| Raji | Burkitt's | 2.0 ± 0.3 | 16 ± 0.8 |
| RL | Transformed follicular | 23.0 ± 2.0 | 210 ± 40 |
| SKI-DLCL-1 | Diffuse large B Cell | 5.1 ± 0.1 | 48 ± 2.5 |

To evaluate cytotoxicity of combination of PDX and GEM, a Trypan Blue Exclusion Assay was performed by aliquoting $5 \times 10^5$ SKI-DLBCL cells into each well of a 24 well plate with a final volume of 1 milliliter. Each drug was added in duplicate to the plate wells as follows: alone (MTX 10 nM, PDX 1 nM, Ara-C 40 nM, or Gem 10 nM), PDX+Gem or MTX+Ara-C for 48 h (hours). For the scheduled administration of drug, PDX or MTX alone were dispensed in additional duplicate wells. After 24 hours Gem and Ara-C were added to these wells, respectively, and incubated for 48 hours. At the end of incubation, 20 l of each cell culture was added to 20 l of trypan blue, after which 10 ml was added to a hemocytometer (Hausser Scientific, Horsham, Pa.), where viable cells were counted based upon the presence (dead cells) or exclusion (live cells) of dye. The results are reported above in Table 1.

Example 3

In order to study the effects of PDX on lymphoma growth in vivo, subcutaneous transplantation models in NOD/SCID mice were generated using three established human lymphoma cell line representative of aggressive transformed FL (RL) and de novo extranodal DLBCL (HT; SKI-DLCL-1) histologies. Six to eight week old non-obsese diabetic severe combined immunodeficient (NOD/SCID) mice (Jackson Laboratories, Bar Harbor, Me.) were sub-lethally irradiated with three cGy from a gamma source and inoculated with $10 \times 10^6$ lymphoma cells via a subcutaneous route. When tumor volumes approached 100 mm$^3$, mice were divided into three groups, averaging 3-8 mice per group. Mice were treated with normal saline or the maximum tolerated dose (MTD) of MTX (40 mg/kg) or PDX (60 mg/kg) via an intraperitoneal route twice weekly for two weeks (four total doses). The MTD of each drug has been previously shown to result in less than 10% weight loss and no toxic deaths in nude mice. (Sirotnak, et al., Cancer Chemother. Pharmacol. 12: 26-30 (1984); Sirotnak et al., Cancer Chemother. Pharmacol. 42: 313-318 (1998).

Engraftment rates in this experiment ranged from 80 to 90%. Palpable tumors formed under the skin approximately 7-10 days after inoculation and were readily measurable with calipers. Mice with subcutaneous lymphoma growths survived an average of 40-50 days after inoculation.

Treatment results in lymphoma xenografted mice are summarized in Tables 4-6. As shown in Table 4 and 5, in the RL (transformed FL) and SKI-DLCL-1 xenografts, PDX treatment resulted in much greater inhibition of lymphoma growth than MTX. These tumors were only minimally sensitive to MTX treatment with small reductions in growth an no regressions. PDX treatment, however, decreased tumor volumes by at least 50% from initial volumes and induced tumor regressions in 57% (5 of 9 mice) and 30% (3 of 10 mice) of RL and SKI-DLCL-1, respectively.

TABLE 4

Treatment of human RL (transformed follicular) non-Hodgkin's lymphoma xenografts

| Agent | Dose (mg/kg) | Weight Change (%) | Avg Tumor Diameter (mm ± SE) | Avg change in Tumor Volume (mm$^3$ ± SE) | Tumor Regression (%) | Complete Regression (no/total) |
|---|---|---|---|---|---|---|
| Control | — | +15.9 | 12.5 ± 1.3 | +1228 ± 238 | — | 0/7 |
| MTX | 40 | −14.8 | 10.9 ± 0.5 | +619 ± 108 | — | 0/12 |
| PDX | 60 | −11.1 | 2.7 ± 1.1 | −46 ± 34 | 56 | 5/9 |

TABLE 5

Treatment of human SKI-DLCL-1 (de novo diffuse large B cell) non-Hodgkin's lymphoma xenografts

| Agent | Dose (mg/kg) | Weight Change (%) | Avg Tumor Diameter (mm ± SE) | Avg change in Tumor Volume (mm$^3$ ± SE) | Tumor Regression (%) | Complete Regression (no/total) |
|---|---|---|---|---|---|---|
| Control | — | +4.9 | 12 ± 0.3 | +786 ± 64 | — | 0/8 |
| MTX | 40 | −1.9 | 9.5 ± 0.4 | +299 ± 58 | — | 0/10 |
| PDX | 60 | −1.2 | 3.5 ± 0.7 | −81 ± 16 | 54 | 3/10 |

As shown in Table 6, even more significant results were achieved using PDX in the treatment of HT xenografts. Although MTX treatment resulted in modest growth delay as compared to controls, there was no tumor regression in these animals. In contrast, PDX administration resulted in complete tumor regression in 89% (8 of 9) of the mice with an average tumor regression of 99%. At the nadir of tumor regression, HL xenograft mice treated with PDX had an average tumor diameter of 0.5 mm, as opposed to 11.2 mm for the control and 8.7 mm for MDX treated mice.

TABLE 6

Treatment of human HT (diffuse large B cell) non-Hodgkin's lymphoma xenografts

| Agent | Dose (mg/kg) | Weight Change (%) | Avg Tumor Diameter (mm ± SE) | Avg change in Tumor Volume (mm³ ± SE) | Tumor Regression (%) | Complete Regression (no/total) |
|---|---|---|---|---|---|---|
| Control | — | +13.2 | 11.2 ± 1.3 | +641 ± 252 | — | 0/8 |
| MTX | 40 | −9.8 | 8.7 ± 2.0 | +300 ± 225 | — | 0/7 |
| PDX | 60 | −8.9 | 0.5 ± 0.3 | −95 ± 0.8 | 99 | 8/9 |

The same type of test was repeated to assess the in vivo efficacy of using combination therapies. Five to seven week old SCID beige mice (CBSCBG-MM double) were obtained from Taconic Laboratories, Germantown, N.Y. Mice were injected with 1×107 SKI-DLBCL cells in the posterior flank via subcutaneous route. When tumors approached 300 mm³, mice were divided into 9 groups of 5 animals and were treated twice weekly with 4 intraperitoneal doses at the MTD of MTX (40 mg/kg), Ara-C (300 mg/kg), PDX (60 mg/kg) and Gem (60 mg/kg), or a combination of the drugs, each given at one half or one-quarter the MTD (20 and 150 mg/kg of MTX and Ara-C, or 15 mg/kg of each of PDX and Gem). Schedule dependent treatment was also determined by pretreating animals with PDX or MTX followed 24 hours later with Gem or Ara-C, respectively. One cohort of animals was treated with Gem followed by PDX. In all cases, the control animals received intraperitoneal injections of normal saline.

Tumor bearing mice were assessed for weight loss and tumor volume at least twice weekly for the duration of the experiment. The data are expressed as the average tumor volume (mm3) per group as a function of time. Tumors were assessed by measuring the two largest perpendicular axes (l=length, w=width) with standard calipers. Tumor volume was calculated using the formula $4/3 \, \pi r^3$ where $r=(l+w)/4$. Tumor bearing mice were assessed for weight loss and tumor volume at least twice weekly for the duration of the experiment. Animals were sacrificed when one dimensional tumor diameter exceeded 2.0 cm, or after loss of more than 10% of their body weight in accordance with institutional guidelines. Animals were housed in standard shoe box cages in temperature and humidity constant rooms on a 12 hour light and dark cycle. Food and water were supplied ad libitum. Animals were maintained in core animal facilities under an institute approved animal protocol. All experiments were performed in accordance with the "Principles of Laboratory Animal Care" (NIH publication No. 85-23 revised 1085).

The results of these experiments are summarized in FIG. 5. In vivo, the combination of PDX and Gem was shown to be superior to any singlet or the MTX/Ara-C combinations. Complete remissions were only observed in animals receiving PDX followed by Gem, however, the model used was the most resistant of the known lymphoma cell lines so better results could be achieved with other cell lines.

Example 4

Immunohistochemical staining for apoptosis as measured by terminal deoxynucleotide transferase-mediated nick end-labeling (TUNEL) was performed on SKI-DLBCL-1 xenografts from mice sacrificed at day 21 following initiation of antifolate therapy. Mice received four doses of saline, MTX (40 mg/kg) or PDX (60 mg/kg) on days 0, 3, 7 and 10. Representative tumors from control and MTX treated mice demonstrated little or no evidence of apoptotic cells. In contrast, systemic treatment with PDX induced a high level of apoptotic cells in the tumor tissue 11 days after the last drug dose. These results confirm the increased cytotoxicity of PDX versus MDX.

To assess apoptosis occurring as a result of combination therapies, apoptosis was assessed using two well standardized techniques. In the first (YO-PRO), cell membrane permeability was determined by measuring fluorescence of treated and control cells. 2×107 SKI-DLBCL cells were treated with either MTX, Ara-C, Gem or PDX alone or combinations of drug given together or scheduled. All drugs were assayed at equimolar concentrations (i.e. 1 nM). The incubation conditions were modeled after the in vitro cytotoxicity experiments. Single agent drugs or combinations of all drugs studied without schedule considerations were incubated for 72 hours, while drugs that were studied in some schedule were introduced in a 24+48 incubation scheme (i.e. drug B added 24 hours following drug A, then incubated for an additional 48 hours for a total incubation time of 72 hours). Cells were then collected, washed twice and re-suspended at a concentration of 1×106/mL in DPBS. Membrane permeability was detected via the differential cellular permeability of the fluorescent dyes YO-PRO®-1 and propidium iodide by flow cytometry, as per the manufacturer's guidelines (Vybrant apoptosis kit #4, Molecular Probes, Eugene, Oreg.). In addition to monitoring apoptosis, cell cycle kinetic analyses were also performed on all treated cells based the propidium iodide binding. Apoptotic cells were noted to be permeable to the green fluorescent dye YO-PRO®-1 (em 530, FL-1), and impermeable to the red fluorescent dye propidium iodide (em 575, FL-3). Typically, apoptotic cells allow the entrance of both dyes, whereas living cells are impermeable to both dyes.

The results of these experiments are summarized in Table 2 above, and show increased apoptosis in cells treated with PDX and Gem than in cells treated with MTX and Ara-C.

Example 5

To further evaluate the activity of PDX and Gem combinations, Caspase activity was tested by EnzChek® Caspase-3 Assay Kit #2 (Molecular Probes) based upon the fluorometric detection of caspase-dependent Z-DEVD-R110 cleavage (rhodamine 110 bis-[N-CBZ-L-aspartyl-L-glutamyl-L-valyl-L-aspartic acid amide], a non-fluorescent bisamide), which, via a two step process, first yields the monoamide product (weakly fluorescent) and then the fluorescent product R110 (rhodamine 110, strongly fluorescent). Detection was performed on a Fluoroskan Ascent FL fluorescent plate reader (Thermo Lab Systems, Helsinki, Finland) according to the manufacturer's guidelines.

The results are summarized in Table 3 above. As shown, there is substantially greater induction of caspase 3 in cells treated with PDX and/or Gem than in those treated with MTX and/or Ara-C.

Example 6

Three proteins are implicated in the metabolism of anti-folates in tumor cells. In most tumor cells, the protein encoded by RFC-1 mediates internalization of folate analogs. Once inside the cell, these analogs either bind dihydrofolate reductase (DHFR), thereby depleting intracellular reduced folate pols needed for purine and thymidine biosynthesis, or will be metabolized to a polyglutamate prior to binding to DHFR. Polyglutamylation is catalyzed by FPGS. FPGH mediates cleavage and clearance of these intracellular polyglutamated anti-folates.

Using quantitative RT-PCR techniques, expression levels were determined in RL, HT and SKI-DCBCL-1 cells lines for RFC-1, FPGS and FPGH using primers described in Rots et al. Leukemia 14:2166-2175 (2000). The results of these determinations are summarized in Table 5. As shown, the HT cell line, which was most sensitive to PDX, also had the greatest levels of RFC-1 expression both on an absolute level and relative to FPGS while the levels of RFC-1 for SKI-DCBCL-1 and RL, which had similar sensitivity to PDX, are similar to one another. Without intending to be bound by a specific mechanism, it is believed that this correlation between RFC-1 expression levels and PDX sensitivity is a reflection of increased transport of PDX into tumor cells. Accordingly, in a further aspect of the invention, sensitivity to PDX and thus the appropriateness of treatment with PDX can be evaluated for a given patient by assessing the amount of RFC-1 expressed in lymphoma cells from the patient.

In accordance with this method of the invention, a lymphoma is assayed for sensitivity to treatment with 10-propargyl-10-deazaminopterin by the steps of:

(a) obtaining a sample of the lymphoma;

(b) determining the amount of reduced folate carrier-1 enzyme (RFC-1) expressed by the sample, wherein a higher level of expressed RFC-1 is indicative of greater sensitivity to 10-propargyl-10-deazaminopterin; and (c) generating a report of the sensitivity of the sample to 10-propargyl-10-deazaminopterin. By way of non-limiting example, the report may be an oral report, a printed report or an electronically transmitted report.

The invention claimed is:

1. A method for treatment of lymphoma comprising administering to a human patient diagnosed as having a lymphoma a composition comprising a therapeutically effective amount of 10-propargyl-10-deazaaminopterin and a therapeutically effective amount of gemcitabine.

2. The method of claim 1, wherein the 10-propargyl-10-deazaaminopterin is substantially free of 10-deazaaminopterin.

3. The method of claim 2, wherein the 10-propargyl-10-deazaaminopterin is administered in an amount of from 30 to 275 mg/m$^2$ per dose.

4. The method of claim 3, wherein the 10-propargyl-10-deazaaminopterin is administered weekly.

5. The method of claim 4, wherein the 10-propargyl-10-deazaaminopterin is administered in a dose of 30 mg/m$^2$.

6. The method of claim 3, wherein the 10-propargyl-10-deazaaminopterin is administered in an amount of from 30 to 150 mg/m$^2$ per dose.

7. The method of claim 1, wherein the 10-propargyl-10-deazaaminopterin is administered biweekly.

8. The method of claim 7, wherein the 10-propargyl-10-deazaaminopterin is administered in a dosage amount of 135 to 275 mg/m$^2$.

9. The method of claim 1, wherein gemcitabine is administered after the 10-propargyl-10-deazaaminopterin.

10. The method of claim 1, wherein the lymphoma is non-Hodgkin's lymphoma.

11. The method of claim 1, wherein the 10-propargyl-10-deazaaminopterin is administered in an amount of from 30 to 275 mg/m$^2$ per dose.

12. The method of claim 11, wherein the 10-propargyl-10-deazaaminopterin is administered weekly.

13. The method of claim 12, wherein the 10-propargyl-10-deazaaminopterin is administered in a dose of 30 mg/m$^2$.

14. The method of claim 11, wherein the 10-propargyl-10-deazaaminopterin is administered in an amount of from 30 to 150 mg/m$^2$ per dose.

15. The method of claim 1, wherein the 10-propargyl-10-deazaaminopterin is administered in an amount of 40 to 120 mg/m$^2$ per day.

* * * * *

UNITED STATES PATENT AND TRADEMARK OFFICE
CERTIFICATE OF CORRECTION

| | | |
|---|---|---|
| PATENT NO. | : 7,939,530 B2 | Page 1 of 1 |
| APPLICATION NO. | : 11/568254 | |
| DATED | : May 10, 2011 | |
| INVENTOR(S) | : Owen O'Connor et al. | |

It is certified that error appears in the above-identified patent and that said Letters Patent is hereby corrected as shown below:

In The Specification

In column 1, beginning at line 13 and ending at line 15, please delete:

"This application was supported by NH grant numbers CA092074 and CA 0172(00). The US government may have certain rights in this invention."

and insert:

--This invention was made with government support under grant numbers CA092074 awarded by National Institutes of Health. The government has certain rights in the invention.--

Signed and Sealed this
Fifth Day of April, 2016

Michelle K. Lee
*Director of the United States Patent and Trademark Office*